(12) United States Patent
Kuracina et al.

(10) Patent No.: US 10,967,101 B2
(45) Date of Patent: Apr. 6, 2021

(54) METHOD AND APPARATUS FOR DIVERTING SWEAT, LIQUID, MOISTURE, OR THE LIKE FROM AN EYE

(71) Applicants: Thomas Charles Kuracina, Minden (NZ); Tim L. Kitchen, San Francisco, CA (US)

(72) Inventors: Thomas Charles Kuracina, Minden (NZ); Tim L. Kitchen, San Francisco, CA (US)

( * ) Notice: Subject to any disclaimer, the term of this patent is extended or adjusted under 35 U.S.C. 154(b) by 514 days.

(21) Appl. No.: 14/610,478

(22) Filed: Jan. 30, 2015

(65) Prior Publication Data
US 2015/0143614 A1 May 28, 2015

Related U.S. Application Data

(60) Division of application No. 13/374,051, filed on Dec. 9, 2011, now abandoned, which is a continuation of
(Continued)

(51) Int. Cl.
*A41D 20/00* (2006.01)
*A42C 5/02* (2006.01)
(Continued)

(52) U.S. Cl.
CPC .............. *A61L 27/54* (2013.01); *A41D 20/00* (2013.01); *A41D 31/12* (2019.02); *A42C 5/02* (2013.01);
(Continued)

(58) Field of Classification Search
CPC ...... A42C 5/02; A41D 20/00; A41D 13/1184; A41D 27/133; A41D 2600/10; A41D 2600/20
(Continued)

(56) References Cited

U.S. PATENT DOCUMENTS 1,907,476 A   5/1933   Ballard
2,001,862 A   5/1935   Battey
(Continued)

FOREIGN PATENT DOCUMENTS

WO    2005025350    3/2005

OTHER PUBLICATIONS

3M Tegaderm IV Transparent Film Dressing1633. Product Booklet [online]. 3M. 2008 [retrieved on Nov. 19, 2013]. Retrieved from the Internet: <URL:http://solutions.3mcanada.ca/3MContentRetrievaiAP 1/BiobServlet?Imd= 1326471206000&locale=en CA&asset-Type=M M M _Image&assetId=1319218638868&blobAllribute= ImageFile >.
(Continued)

*Primary Examiner* — Sally Haden
(74) *Attorney, Agent, or Firm* — Edell, Shapiro & Finnan, LLC

(57) ABSTRACT

Moisture diverters attachable to a region above the eye and below the eyebrow that prevents sweat, liquid, moisture, or the like from entering the eyes of a wearer is described. A moisture diverter may include a substrate having an inner surface facing the wearer and an outer surface facing away from the wearer. The inner surface comprises a lower adhesive section and an upper adhesive-free section, the adhesive section releasably attaches the diverter to the wearer at a point above the eye and below the eyebrow, the adhesive-free section shaped or shapeable to abut or protrude from eyebrow region of a wearer and to divert moisture away from the eye.

3 Claims, 5 Drawing Sheets

Related U.S. Application Data application No. 11/872,031, filed on Oct. 14, 2007, now abandoned.

(60) Provisional application No. 60/852,100, filed on Oct. 13, 2006.

(51) Int. Cl.
    *A61L 27/54*     (2006.01)
    *A41D 31/12*     (2019.01)
    *A61K 33/42*     (2006.01)
    *A61L 27/12*     (2006.01)
    *A61L 27/20*     (2006.01)
    *A61L 27/22*     (2006.01)
    *A41D 13/11*     (2006.01)

(52) U.S. Cl.
CPC .............. *A61K 33/42* (2013.01); *A61L 27/12* (2013.01); *A61L 27/20* (2013.01); *A61L 27/222* (2013.01); *A41D 13/1184* (2013.01); *A61L 2430/02* (2013.01); *Y10T 156/10* (2015.01)

(58) Field of Classification Search
USPC ............. 2/410, 424, 15, 11, 12, 9, 171, 181, 2/182.3, 174; 132/215, 216, 217
See application file for complete search history.

(56) References Cited

U.S. PATENT DOCUMENTS

| | | |
|---|---|---|
| 2,572,638 A | 10/1951 | Loos |
| 2,783,474 A | 3/1957 | Campagan et al. |
| 2,842,142 A | 7/1958 | Peck |
| 2,862,509 A | 12/1958 | Porte |
| 3,068,863 A | 12/1962 | Bowman |
| 3,092,103 A | 6/1963 | Mower |
| 3,266,500 A | 8/1966 | Weld |
| 3,485,251 A | 12/1969 | Brunet |
| 3,568,684 A | 11/1971 | Reece |
| 3,619,815 A | 11/1971 | Towner, Jr. |
| 3,668,050 A | 6/1972 | Donnelly |
| 3,823,723 A | 7/1974 | Miller |
| 3,949,741 A | 4/1976 | Hofmann |
| 4,024,879 A | 5/1977 | Stryker |
| 4,432,347 A | 2/1984 | Calvin |
| 4,521,922 A | 6/1985 | Mitchell et al. |
| 4,599,746 A | 7/1986 | Stoner |
| 4,626,247 A | 12/1986 | Frankel |
| 4,638,512 A | 1/1987 | Frankel |
| 4,653,483 A | 3/1987 | Calvin |
| 4,709,695 A | 12/1987 | Kohn et al. |
| 4,719,909 A | 1/1988 | Micchia et al. |
| 4,776,042 A | 10/1988 | Hanson et al. |
| 4,793,003 A | 12/1988 | Riedel et al. |
| 4,807,650 A | 2/1989 | Bliss |
| 4,862,902 A | 9/1989 | Goffman |
| 4,867,146 A | 9/1989 | Krupnick et al. |
| 4,936,325 A | 6/1990 | Davis |
| 4,942,891 A | 7/1990 | Trevisan |
| 4,944,040 A | 7/1990 | Riedel et al. |
| 4,958,385 A | 9/1990 | Rushton, Jr. |
| 4,966,168 A * | 10/1990 | Glassman .............. A61B 46/00 128/849 |
| 4,979,811 A | 12/1990 | Boyer |
| 4,995,114 A | 2/1991 | Price, Jr. |
| 5,140,997 A * | 8/1992 | Glassman .............. A61B 46/00 128/849 |
| 5,144,944 A | 9/1992 | Rice |
| 5,191,897 A | 3/1993 | Meshel |
| 5,263,200 A | 11/1993 | Miller |
| 5,317,761 A | 6/1994 | Piche |
| D355,489 S | 2/1995 | Almond |
| 5,592,687 A | 1/1997 | Lajeunesse |
| 5,765,231 A | 6/1998 | Leonard et al. |
| 5,781,932 A | 7/1998 | Brown |
| 5,887,590 A | 3/1999 | Price |
| 5,970,515 A | 10/1999 | Fishbaugh |
| 6,012,171 A | 1/2000 | Altman |
| 6,034,293 A | 3/2000 | Stamler |
| 6,052,825 A | 4/2000 | Dodd |
| 6,105,579 A | 8/2000 | Levitt et al. |
| 6,108,818 A | 8/2000 | Eisenberg |
| 6,131,208 A | 10/2000 | Banks |
| 6,161,554 A | 12/2000 | Dunlap-Harris |
| 6,190,346 B1 | 2/2001 | McGill |
| 6,193,741 B1 | 2/2001 | Heavenridge et al. |
| D440,315 S | 4/2001 | Hassenbein et al. |
| 6,286,511 B1 | 9/2001 | Levitt et al. |
| 6,336,462 B1 | 1/2002 | Santelli et al. |
| 6,350,338 B1 | 2/2002 | Comiskey et al. |
| 6,353,936 B2 | 3/2002 | Flatt |
| 6,405,730 B2 | 6/2002 | Levitt et al. |
| 6,481,021 B1 | 11/2002 | Spell |
| 6,574,801 B1 | 6/2003 | Harens et al. |
| RE38,246 E | 9/2003 | Leonard et al. |
| 6,623,517 B1 | 9/2003 | Deluisa et al. |
| 6,632,499 B1 | 10/2003 | Marks, III et al. |
| 6,640,814 B1 | 11/2003 | Burke |
| 6,733,856 B2 | 5/2004 | Nojiri |
| 6,789,272 B2 | 9/2004 | Thorson |
| D507,350 S | 7/2005 | Mueller et al. |
| D507,651 S | 7/2005 | Mueller et al. |
| D511,573 S | 11/2005 | Mueller et al. |
| 6,971,122 B2 | 12/2005 | Sanchez |
| 6,984,037 B2 | 1/2006 | Bleau |
| 7,011,401 B2 | 3/2006 | Markey, III |
| 7,052,130 B2 | 5/2006 | Fishbaugh |
| 7,093,303 B2 | 8/2006 | Thorson |
| D527,824 S | 9/2006 | Mueller et al. |
| 7,188,946 B2 | 3/2007 | Bleau |
| 7,275,819 B2 | 10/2007 | Bleau |
| 7,322,991 B1 | 1/2008 | Robinson |
| 7,398,559 B2 | 7/2008 | Flatt |
| 7,496,968 B2 | 3/2009 | Head |
| 7,648,430 B2 | 1/2010 | Gagnon |
| 7,681,252 B1 | 3/2010 | Petry |
| 7,703,148 B2 | 4/2010 | Bowers |
| 8,074,667 B2 | 12/2011 | Villanueva |
| 8,166,772 B2 | 5/2012 | Cho |
| D669,637 S | 10/2012 | Endsley |
| 8,333,205 B2 | 12/2012 | Haddad |
| D694,955 S | 12/2013 | Gallina |
| 9,009,869 B1 * | 4/2015 | Shapiro .................. A41D 31/00 2/181 |
| 9,565,887 B2 * | 2/2017 | Shapiro .................. A41D 20/00 |
| 2001/0047536 A1 | 12/2001 | Flatt |
| 2002/0000232 A1 | 1/2002 | Levitt |
| 2002/0100481 A1 * | 8/2002 | Abbasi ...................... A61F 9/04 128/858 |
| 2002/0108615 A1 | 8/2002 | Levitt |
| 2002/0138896 A1 | 10/2002 | Holden |
| 2003/0221236 A1 | 12/2003 | Hippensteel |
| 2004/0006814 A1 | 1/2004 | Holden |
| 2004/0107483 A1 | 6/2004 | Thorson |
| 2004/0218140 A1 | 11/2004 | Bleau |
| 2005/0217688 A1 | 10/2005 | Liu |
| 2006/0013844 A1 | 1/2006 | Meriaux |
| 2006/0070161 A1 | 4/2006 | Bleau |
| 2007/0044204 A1 | 3/2007 | Kelly |
| 2007/0079423 A1 | 4/2007 | Flatt |
| 2007/0295353 A1 | 12/2007 | Dinh |
| 2008/0066212 A1 | 3/2008 | Holden |
| 2008/0086792 A1 | 4/2008 | Kuracina et al. |
| 2008/0216214 A1 | 9/2008 | Dolby |
| 2008/0263751 A1 | 10/2008 | Flatt |
| 2009/0077716 A1 * | 3/2009 | Farney ..................... A42C 5/02 2/181 |
| 2009/0100558 A1 | 4/2009 | Smith |
| 2009/0151744 A1 | 6/2009 | Villanueva |
| 2009/0183750 A1 | 7/2009 | Platt-Gregory |
| 2009/0235950 A1 * | 9/2009 | Dinh ........................ A41G 5/02 132/216 |

(56) References Cited

U.S. PATENT DOCUMENTS

| | | |
|---|---|---|
| 2009/0277451 A1 | 11/2009 | Weinberg |
| 2010/0018542 A1 | 1/2010 | Konrad |
| 2010/0154813 A1 | 6/2010 | Deeds |
| 2010/0263247 A1 | 10/2010 | Liguori |
| 2011/0088716 A1 | 4/2011 | Villanueva |
| 2012/0312445 A1 | 12/2012 | Kuracina et al. |
| 2014/0289932 A1* | 10/2014 | Shapiro .................. A41D 20/00 2/181 |

OTHER PUBLICATIONS

Appendix A. 3M Product Catalog at HTTP://solutions.3m.com/wps/portal/3M/en_US/oem/MedicaiOEM/product-info/catalog/?PC_7RJH9U52300EPD0IMMDBBVN1EG4000000_nid=DZMFHCQPXGbe5CZVR8 MZNCgl; 3M Steri-Drapes Ophthalmic Surgical Drapes with Aperture; Dec. 2, 2011 (dale accessed and downloaded), pp. 1-3, 3M, St. Paul, Minnesota.

Appendix B, 3M Surgical Drapes, Gowns and Custom Procedure Trays Range Guide at http://multimedia.3m.com/mws/mediawebserver?mwsld=66666UuZjcFSLXTIMxTXIX M_EVuQEcuZgVs6EVs6E666666--; 3M Asepsis Products, © 3M Health Care Limited 2006 (the year of publication is sufficiently earlier than the effective U.S. filing date and any foreign priority date so that the particular month of publication is not in issue) (Dec. 2, 2011 date accessed and downloaded) pp. 1-87, Loughborough Leicestershire, England, Dublin, Ireland, and St. Paul, MN, USA.

Appendix C, The Medical Supply Group Model 1020 Product Detail Information at http://www.medicalsupplygroup.com/PERSONAL_PROTECT-GLOVES/PHYSICIAN_SUPPLIES/MMM1020/product.aspx; 3M TM Steri-Drape TM- Surgical Drape with Aperture, Dec. 2, 2011 (date accessed and downloaded), pp. 1-3; © 2003-2011 Medical Supply Group, Deerfield Beach, Florida.

Appendix A. 3M Product Catalog at HTTP://solutions.3m.com/wps/portal/3M/en_US/oem/MedicaiOEM/product-info/catalog/?PC_7RJH9U52300EPD0IMMDBBVN1EG4000000_nid=DZMFHCQPXGbe5CZVR8 MZNCgl; 3M Steri-Drapes Ophthalmic Surgical Drapes with Aperture; Aug. 8, 2013 (date accessed and downloaded), pp. 1-3, 3M, St. Paul, Minnesota.

Appendix B, 3M Surgical Drapes, Gowns and Custom Procedure Trays Range Guide at http://multimedia.3m.com/mws/mediawebserver?mwsld=66666UuZjcFSLXTIMxTXIX M_EVuQEcuZgVs6EVs6E666666--; 3M Asepsis Products, © 3M Health Care Limited 2006 (the year of publication is sufficiently earlier than the effective U.S. filing dale and any foreign priority date so that the particular month of publication is not in issue) (Aug. 8, 2013 date accessed and downloaded) pp. 1-87, Loughborough Leicestershire, England, Dublin, Ireland, and St. Paul, MN, USA.

Appendix C, The Medical Supply Group Model 1020 Product Detail Information at http://www.medicalsupplygroup.com/PERSONAL_PROTECT-GLOVES/PHYSICIAN_SUPPLIES/MMM1020/product.aspx; 3M TM Steri-Drape TM- Surgical Drape with Aperture, Aug. 8, 2013 (date accessed and downloaded), pp. 1-3; © 2003-2011 Medical Supply Group, Deerfield Beach, Florida.

* cited by examiner

METHOD AND APPARATUS FOR DIVERTING SWEAT, LIQUID, MOISTURE, OR THE LIKE FROM AN EYE

CROSS REFERENCE TO RELATED APPLICATIONS

This application is a divisional of U.S. patent application Ser. No. 13/374,051 filed Dec. 9, 2011, entitled "Method and Apparatus for Diverting Sweat, Liquid, Moisture, or the Like from an Eye," which is a continuation of U.S. patent application Ser. No. 11/872,031 filed Oct. 14, 2007, entitled "Method and Apparatus for Diverting Sweat, Liquid, Moisture, or the Like from the Eye," now abandoned, which claims benefit of U.S. Provisional Application No. 60/852,100, filed Oct. 13, 2006, and entitled "Method and Apparatus for Diverting Sweat from an Eye," the entire contents of which are hereby incorporated by reference.

FIELD OF THE INVENTION

The present invention relates generally to an apparatus for diverting, redirecting or channeling sweat, perspiration, liquid (such as rain) or moisture (skinborne or other) away from the eye or eyes.

BACKGROUND

Living organisms require nutrients and water and give off waste from the metabolic processes. Strenuous activity increases metabolism and increases body core temperature where the body loses liquid through the lungs and skin. A thermal cooling effect is created when sweat is produced and evaporates from the skin. This mechanism is crucial in the regulation of body temperature. The surface area of the head and face contain sweat glands and produce perspiration that can collect and drip into the eye or eyes, obscuring one's ability to see clearly.

A number of known devices have been used in an attempt to keep sweat from dripping into or entering the eye or eyes, like sweatbands, hats with an absorbent browband and even eyeglass perspiration guards. Many of these devices are disposable and include an absorbent member. The main disadvantages of these prior art inventions are that they do not address the area below the eyebrow, are used mainly on the forehead, are meant to absorb sweat and when these products reach a certain saturation point of liquid absorption, they no longer perform as intended and allow excess sweat or perspiration to enter the eye or eyes. Sweat entering the eyes impairs the vision of surgeons, firefighters, police, athletes, military personnel, construction workers, tree trimmers, loggers and others who are involved in activities where clear vision is imperative to perform the task at hand and many times both hands are needed to perform that task. In addition to wearing an absorbent headband, some athletes also wear absorbent wristbands to wipe perspiration that gets past the headband and into the eye or eyes.

Headbands saturated with sweat also become heavy and sag, requiring the user to repeatedly adjust the apparatus from slipping lower on the head.

Some examples of these inventions are taught by Brown in U.S. Pat. No. 703,531, where an eye guard worn upon the forehead prevents perspiration from running into the eyes. In U.S. Pat. No. 1,084,596, Alexander teaches a perspiration band for headgear that includes a hollow tape and stiffening strip. In U.S. Pat. No. 4,626,247, Frankel teaches a sweat collecting headband worn on the forehead that channels the sweat to the runner's mouth. In U.S. Pat. No. 7,093,303, Thorson teaches a liquid absorbing component attached to eyeglasses. All of these inventions fail to address the sub eyebrow region or orbit of the eye. What is needed is a low cost, simple apparatus that contacts the skin and creates a liquid tight seal and diverting apparatus above the eye and below the brow, or above the eye and over the brow.

The diverting apparatus of the present invention directs movement of sweat or moisture away from the wearer's eye or eyes, maintaining optimum visual clarity, especially during strenuous activity. The present invention may also be used on animals such as racehorses or in instances where sweat or insects may hinder activity or vision.

Despite all the obvious inadequacies associated with the use of headbands or the like, no functional alternative exists that addresses the use of a light-weight moisture diverter that is attachable to a region above the eye and below the eyebrow of a wearer.

What is needed is a low-cost, sweat, liquid, moisture diverting apparatus that is easily manufactured and prevents sweat, liquid, moisture, or the like from entering the eye or eyes of the wearer.

SUMMARY

In accordance with one embodiment, the present invention provides a diverting apparatus comprising a substrate comprising an inner surface and an outer surface, the inner surface comprising a lower section and an upper section, the lower section comprising an adhesive useable for releasably attaching the diverting apparatus to a wearer in a region above the eye and below the eyebrow of the wearer, the upper section shaped or shapeable to abut or protrude from the eyebrow region of the wearer to divert sweat, liquid, moisture, or the like away from the eye.

In another embodiment a diverting apparatus for diverting sweat, liquid, moisture, or the like from both eyes of a wearer includes a right eye diverter, a left eye diverter and a middle section joining the right and left eye diverters, each of the right eye and left eye diverters comprising a substrate comprising an inner surface and an outer surface, the inner surface comprising a lower section and an upper section, the lower section comprising an adhesive useable for releasably attaching the diverting apparatus to a wearer in a region above the eye and below the eyebrow of the wearer, the upper section shaped or shapeable to abut or protrude from the eyebrow region of the wearer to divert sweat, liquid, moisture, or the like away from the eye A method for fabricating a moisture diverting device that is releasably attachable to a region above the eye and below the eyebrow of a wearer is also provided, the method comprising shaping a substrate that comprises an outer surface and an inner surface, the inner surface having an upper section and a lower section, the upper and lower sections each having an adhesive surface covering at least a portion thereof, the outer surface having an adhesive-free upper section located opposite the upper section of the inner surface, the substrate being shaped so that the moisture diverting apparatus is conformable to be worn at a region directly above the eye of the wearer when the fabrication method is complete; and folding back the adhesive-free upper section of the outer surface to create an adhesive-free upper portion on the inner surface.

It is therefore an object of the present invention to provide a moisture diverting apparatus that effectively prevents perspiration from entering the eye or eyes.

It is an additional object of the present invention to provide a moisture diverting apparatus that is gas permeable, allowing the skin of the wearer to breathe.

It is a further object of the present invention to provide a moisture diverting apparatus that creates a liquid tight seal above the eye and below the eyebrow of a wearer.

It is still another object of the present invention to provide a moisture diverting apparatus that comprises a projecting portion, rim, ledge, channel, or the like for channeling or wicking moisture or liquid away from an eye or the eyes.

It is another object of the present invention to provide a moisture diverting apparatus having a surface that includes an adhesive portion for attachment to the skin and another portion that is adhesive free and prevents adhesion to a specific area of skin or hair of the wearer.

It is a further object of the present invention to provide a moisture diverting apparatus that includes a peelable liner that is removably attached to the adhesive portion of said apparatus to maintain adhesive tack during manufacture, packaging, shipment or storage prior to use It is another object of the present invention to provide a moisture diverting apparatus that is low cost and single-use in nature.

It is an additional object of the present invention to provide a moisture diverting apparatus that can be removably attached over an individual eye.

It is an additional object of the present invention to provide a moisture diverting apparatus that can be removably attached over both eyes.

It is a further object of the present invention to provide a moisture diverting apparatus that can assists in shading an eye or the both eyes.

It is another object of the present invention to provide a moisture diverting apparatus that includes an indicia, logo or the like to identify an association as a member, supporter or fan of an organization or team or for ornamental or advertising purposes. The moisture diverting apparatus may also include a camouflage surface for military personnel and snipers.

It is another object of the present invention to provide a moisture diverting apparatus that can be removably attached to the skin adjacent the eye or eyes.

It is still another object of the present invention to provide a moisture diverting apparatus that can be removed and reattached to the skin adjacent the eye or eyes.

It is still another object of the present invention to provide a moisture diverting apparatus that automatically diverts sweat, liquid, perspiration, moisture, or the like to the side of the head or other region away from the eye or eyes.

It is still another object of the present invention to provide a moisture diverting apparatus that automatically diverts sweat, liquid, perspiration, moisture or the like to the middle of the face and away from the eye or eyes.

It is another object of the present invention to provide a moisture diverting apparatus wherein at least a portion is transparent, partially transparent, opaque, or the like when worn allowing the wearer's skin and eye brows to be seen.

It is an additional object of the present invention to provide a moisture diverting apparatus that lends itself to high volume, automated manufacturing.

It is another object of the invention to provide a moisture diverting apparatus that includes one or more reinforcing members to assist in maintaining the shape of the apparatus before and/or after being applied to the wearer.

It is another object of the invention to provide a moisture diverting apparatus where an adhesive portion and non-adhesive portion is fabricated on the same face by folding a portion of the adhesive section over itself and sealing the two sections together to form the non-adhesive portion.

It is an additional object of the present invention to provide a moisture diverting apparatus that includes a recessed channel or groove to assist in diverting liquid away from an eye or the eyes.

It is a further object of the present invention to provide a means to wick liquid away from the eye or eyes.

It is another object of the present invention to provide a moisture diverting apparatus that is sterile for use in operating rooms, dental and surgical procedures, and general medical use.

It is an additional object of the present invention to provide a moisture diverting apparatus that can be adjusted to fit a variety of wearers by removing a portion of the apparatus to adjust one or more dimensional characteristics (e.g., length, width, curvature).

In an embodiment the moisture diverting apparatus of the present invention includes an adhesive surface, film or coating that is attachable to the skin adjacent the eye or eyes.

In an embodiment the moisture diverting apparatus of the present invention includes a reinforcing member or members that can be manipulated to maintain a shape to direct liquid away from the eyes.

In an embodiment the moisture diverting apparatus of the present invention includes a member that includes an absorbent material that is attached to said member for absorbing moisture.

In another embodiment the moisture diverting apparatus of the present invention may include a plurality of perforations to assist in fluid evaporation and body temperature regulation.

Other objects and benefits of this invention will become apparent from the description which follows hereinafter when read in conjunction with the figures that accompany it.

DETAILED DESCRIPTION

A moisture diverting apparatus to prevent perspiration, sweat, liquid, moisture, and the like from entering the eye or eyes is described. In the following description, numerous specific details are set forth in order to provide a thorough understanding of the present invention. However, it will be obvious to one of ordinary skill in the art that the invention may be practiced without these specific details. In other instances, well-known structures and processing steps have not been shown in particular detail in order to avoid unnecessarily obscuring the present invention. Additionally, it should be noted that throughout this discussion reference will be made to a variety of members, shapes, sizes and adhesives. It is appreciated, however, that the present invention is not limited to these devices or materials. Further, throughout the description the diverting apparati are referred to as sweat diverters. It is to be understood, however, that the diverter apparati of the present invention are not limited to diverting sweat but are useful in diverting all forms of moisture and liquids from the eyes of the wearer.

Figure 1:
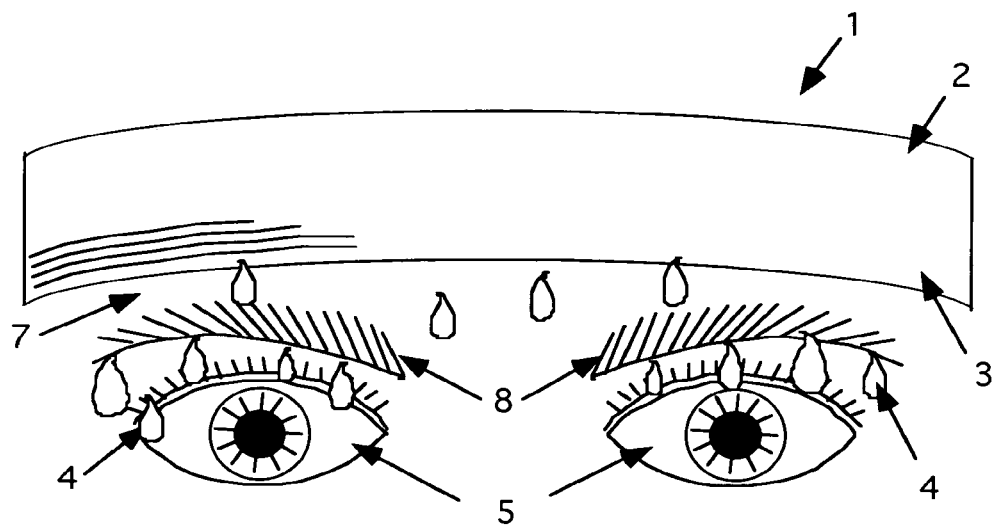
FIG. 1 illustrates a frontal view of a prior art headband allowing sweat or perspiration to enter the eye or eyes.

FIG. 1 is a full frontal view drawing of a prior art standard headband 1, having top 2 and bottom 3 comprising an absorbent material with elastomeric properties to fit circumferentially and snugly around the head. When headband 1 becomes saturated with liquid, any excess moisture, bodily fluid, or sweat 4 moves toward the eyes 5 by gravitational force or by any moving force exerted by the individual or animal. Headband 1 only absorbs the moisture it comes in contact with or is created from the area above it, so brow area 7 between headband bottom 3 of eye or eyes 5 is left exposed and prone to allow sweat 4 to enter said eye or eyes 5.

Figure 2A:
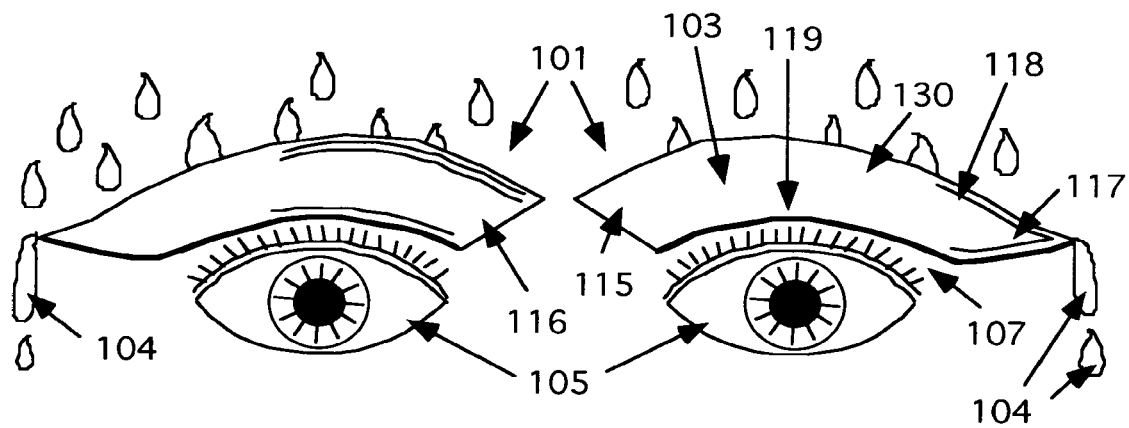
FIG. 2A is a frontal view of an attachable moisture diverting apparatus of the present invention having an arcuate or curved configuration and shown covering the upper orbit, or a portion thereof, of each eye and extending upward toward the eyebrow of a wearer and configured to divert moisture away from the eyes.

FIG. 2A is a full frontal view drawing of the sweat diverting apparatus of the present invention showing a separate sweat diverting apparatus 101 individually covering, or partially covering, the upper orbit 107 of each eye 105. The sweat diverter extends upward to a location below, at, or above the eyebrow of the wearer and acts to divert sweat, liquids, moisture, or the like away from eyes 105. Sweat diverting apparatus 101 comprises a substrate 130 having an exterior face 103, a top section 118 that is designed to protrude slightly from the brow of the wearer and creates a channel to divert any accumulated moisture away from each eye 105 (See FIGS. 13 and 14). The substrate also comprises a bottom section 119, bridge or inner section 115 and opposite outer section 117, bottom section 119 having an adhesive 111 for attachment to the skin. Although not necessary, substrate 130 preferably comprises a material that does not absorb liquid. As shown, the sweat diverting apparatus 101 is releasably attachable to orbit 107 adjacent to eye or eyes 105. As mentioned above, the sweat diverting apparatus of the present invention may also be attachable around the entire orbit or eye, or any portion thereof to prevent sweat from entering the eye or to reduce glare. Moreover, it is important to note that the sweat diverting apparatus of the present invention may comprise a variety of shapes including rectangular, arcuate, curved, longitudinal or any other shape that will allow attachment to the skin above the eye or eyes.

Sweat diverting apparatus 101 may also comprise a decorative shape or shapes, ornamental artwork or logo to coordinate and identify an association with a team, mascot, brand, event or the like. A "mirror" configuration shape of sweat diverting apparatus 101 is shown releasably attached above both eyes individually. A tab or protrusion (not shown) may also be included to facilitate removal of sweat diverting apparatus 101 from the skin. The substrate may include a plurality of perforations, allowing the skin to breathe when sweat diverting apparatus 101 is attached to the skin.

Figure 2B:
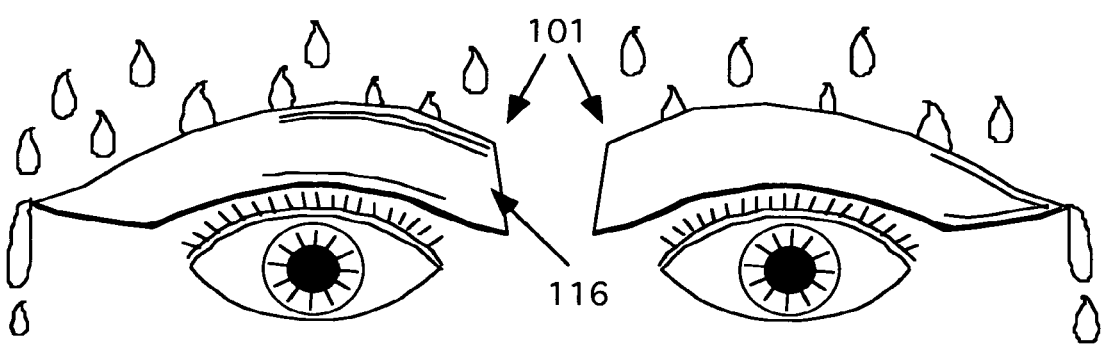
FIG. 2B is a frontal view of another embodiment of the present invention.

In FIG. 2, a bridge section 115 is shown having an edge 116 that slopes inward toward the eye 105. FIG. 2B shows an alternative embodiment wherein edge 116 slopes outward and downward from the brow region. The outward sloping edge configuration of FIG. 2B ensures that any moisture droplets that form along edge 116 will fall away from eyes 105.

The skin of the eyelids essentially extends from the eyelashes to under the eyebrow. The skin surface of this region is the thinnest epidermis on the body (approximately 0.5 mm) and comprises skin, hair (eyelashes), lacrimal (tear) glands, blood vessels and connective tissue. Capillary blood vessels under the skin supply nutrients and oxygen, and also help to regulate the temperature of the eyelid area. These capillaries are connected to the vein that supplies blood to the brain. Therefore, thermal cooling can be regulated by the vasculature. Compared with other skin areas, the eyelid region has a low concentration of ecrine sweat glands, making attachment of a liquid diverting strip having a liquid-tight, adhesive bond possible. The highest concentration of eccrine glands are on hairy skin surfaces, respond to thermal stimulation, and provide cooling.

In accordance with one aspect of the present invention the diverting apparatus 101 preferably comprises a pressure sensitive adhesive 111 having the following characteristics: (1) an aggressive and permanent tack; (2) requires no activation by an outside energy source; (3) has sufficient ability to bond onto the adherend skin; (4) has sufficient cohesive strength to be removed cleanly from the skin; and (5) allows painless and easy removal without damaging the skin. Preferably an adhesive that instantly interacts with skin surface lipids, providing mechanical flow into the valleys of the rough surface of the skin and adheres to the keratin. Examples of adhesives for use in a diverting apparatus of the present invention are acrylic-based adhesives (monomers and polar monomers or a combination thereof), polymer-based adhesives, uncrosslinked elastomeric polymers, synthetic rubber-based adhesives, hydrocolloid absorbent adhesives and silicone-based adhesives. An advantage of the aforementioned adhesives is that they are stable enough to be sterilized for medical use and maintain the desired skin adhesion characteristics. An adhesive widely used for medical applications includes acrylate monomers (esters which contain vinyl groups, that is, two carbon atoms double-bonded to each other, directly attached to the carbonyl carbon).

The sweat diverting apparatus substrate that carries the adhesive may include a high-moisture vapor-transmission rate (MVTR) material that is gas permeable, allowing bodily fluids to evaporate. A non-porous substrate with perforations to allow the skin to "breathe", may also be used. The adhesive and substrate may also be latex-free and hypoallergenic. Both polyurethane and incise film substrates are gas permeable without being perforated. A pattern-coated adhesive may also be used to achieve high MVTR.

The thickness of the adhesive depends on the materials being used. An adhesive thickness of 0.8 mil-1.0 mil for an acrylate adhesive is desirable on a polyethylene substrate. The polyethylene substrate can range in thickness between 6 and 10 mil. and is sufficient to maintain enough rigidity to support a projecting ledge beyond the eyebrow without fatiguing when channeling liquid to the side of the face. This projecting ledge creates a channel at the base of the forehead and collects and diverts any liquid that rolls or drips down above the eyebrows away from the eye, maintaining unobstructed vision for the user.

Figure 3:
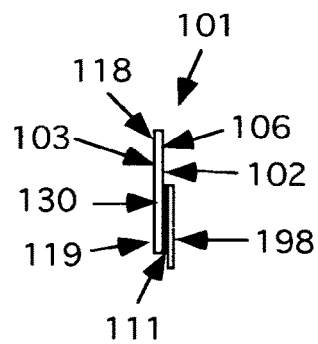
FIG. 3 is a side view of the moisture diverting apparatus shown in either FIG. 2A or FIG. 2B having an adhesive-free outer surface and an inner surface having an adhesive portion and an adhesive-free portion.

FIG. 3 is a side view drawing of the sweat diverters shown in either of FIG. 2A or 2B of the present invention comprising substrate 130 having outer face 103, top section 118, bottom section 119, back or inner surface 102 that includes an adhesive surface, film or coating 111 for releasably attaching diverting apparatus 101 to the skin adjacent the eye or eyes. Top portion 106 is designed to abut the eyebrow area and does not contain adhesive so the eyebrow hair will remain intact when sweat diverting apparatus 101 is removed from the skin. A liner 198 may be removably attached to adhesive portion 111 to maintain adhesive tack during manufacture, handling, packaging, shipping or storage until ready for use. If used, liner 198 may comprise a thin layer of silicone. Top portion 106 may comprise a coating that assists in diverting moisture, such as, for example, a lubricious coating. Other coatings, such as medicants, may also be applied to one or more surfaces of the sweat diverter or impregnated within the components/materials used in constructing the diverter. FIG. 3 is side view of FIG. 4 shown in axis 3-3.

Figure 4:
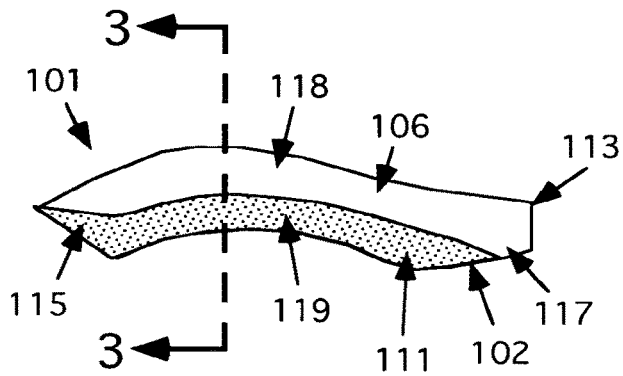
FIG. 4 is a rear view of the moisture diverting apparatus of the present invention of FIG. 3 shown in axis 3-3.

FIG. 4 is a rear of the sweat diverting apparatus 101 of FIGS. 2A and 3 comprising top section 118 that is designed to protrude slightly from the brow of the wearer and creates a channel to divert any accumulated moisture away from each eye 105 (See FIGS. 13 and 14), bottom section 119, side section 115 and opposite side section 117 with a protrusion, corner or edge 113 for easy removal from the skin, rear or inner surface 102 having an adhesive surface or coating 111 on lower portion 119 for releasably attaching said sweat diverting apparatus 101 to the skin adjacent to the eye or eyes. Upper portion 118 having adhesive free surface 106 to keep eyebrow hair intact during attachment, use and removal.

Figure 5:
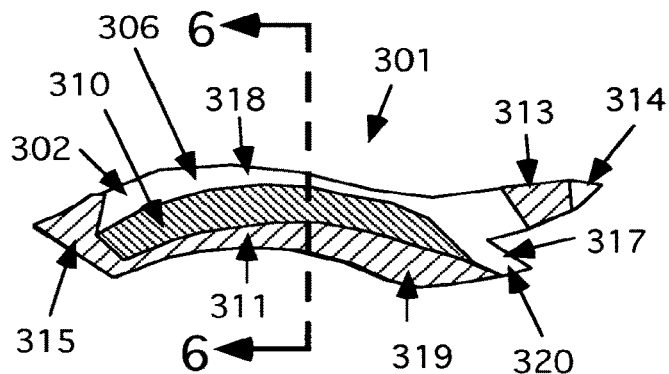
FIG. 5 is a rear view of a moisture diverting apparatus of the present invention sized to fit the contour of the orbit of the eye having an absorbent portion, an adhesive portion, an adhesive free portion for diverting moisture away from the eye, and an extending portion comprising adhesive to assist in maintaining said apparatus in place.

FIG. 5 is a rear view drawing of a sweat diverting apparatus 301 of the present invention shaped to fit the contour of the orbit of the right eye comprising top section 318, bottom section 319, side section 315, an opposite side section 317, and a rear or inner surface 302 designed to contact the skin of the wearer. Bottom section 319 comprising portion with an adhesive 311 for releasably attaching sweat diverting apparatus 301 to an area adjacent an eye, top section 318 having an adhesive-free portion 306 that may include an absorbent or porous material 310 for collecting, channeling or diverting moisture or sweat away from an eye, an exit path or route 320 to direct sweat away from an eye, and protrusion 314 to assist in keeping said diverting apparatus in place and adjacent the eye or eyes. Adhesive 311 on inner surface portion 302 seals sweat diverting apparatus 301 to the skin below the eyebrow and prevents moisture or sweat from penetrating the adhesive barrier and entering the eye or eyes. Protrusion 314 may also aid in increasing the ocular aperture opening by the elevating and stretching skin above the eye and securing it to the forehead. Protrusion 314 may include an adhesive portion 313 and an outer portion that is adhesive free for easy removal of sweat diverting apparatus 301.

Figure 6:
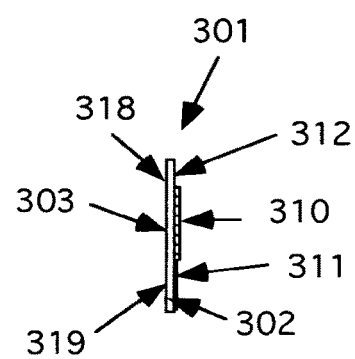
FIG. 6 is a side view of the moisture diverting apparatus of the present invention of FIG. 5 shown in axis 6-6.

FIG. 6 is a side view drawing of FIG. 5, shown in axis 6-6, comprising sweat diverting apparatus 301 having top section 318, bottom section 319, front or outer surface 303, rear or inner surface 302 having a portion with an adhesive means 311, an adhesive-free portion 306, and an absorbent section or member 310. Member 310 may also comprise a material that is not absorbent and repels any sweat it comes in contact with and may act as a cushioning or shock-absorbing member in the event of an impact to the area.

Figure 7:
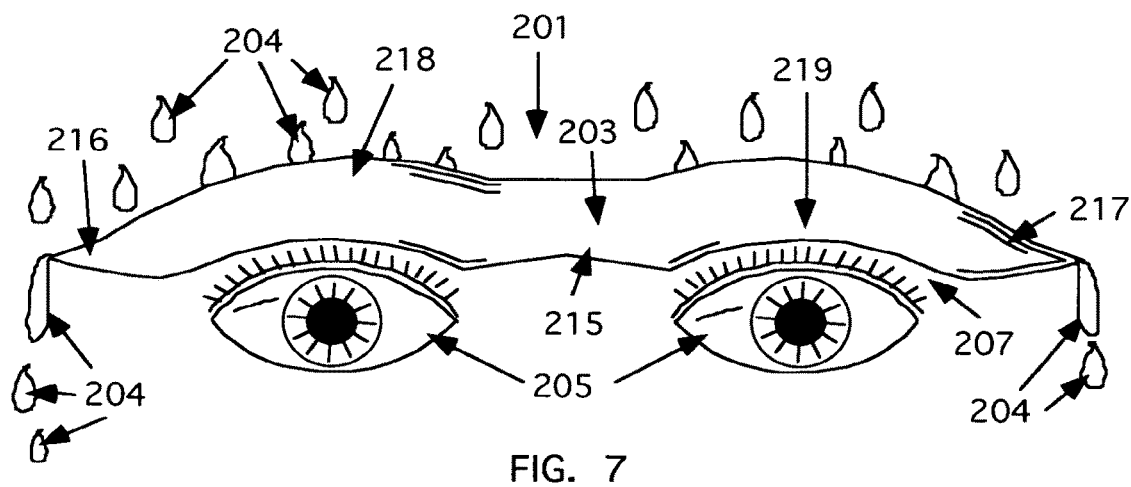
FIG. 7 is a frontal view a one piece, moisture diverting apparatus of the present invention sized to fit the contour of the orbit of both eyes.

FIG. 7 is a frontal view of another embodiment of the present invention comprising a unitary sweat diverting apparatus 201 that is releasable attachable to the facial area 207 or orbit above both eyes 205 for diverting sweat or moisture 204 away from said eyes 205. Diverting apparatus 201 spans the orbit of both eyes and includes an adhesive-free front or outer surface 203, side section 216, opposite side section 217, top section 218, bottom section 219, intermediate bridge, middle or "unibrow" section 215. Diverting apparatus 201 is releasably attachable to a wearer's face directly adjacent the eyes. Diverting apparatus 201 is shown covering the upper orbit of each eye, or a portion thereof. Sweat diverter 201 extends upward to a location below, at, or above the eyebrow of the wearer. Diverting apparatus 201 may be manufactured to contact only the upper orbit of each eye, and not the eyebrows. The embodiment of the FIG. 7 insures any sweat from the middle of the forehead is diverted to the side of the head and away from the wearer's eyes. Diverting apparatus 201 may comprise an absorbent material that may also include adhesive properties, or of a non-absorbent material that may also include adhesive properties.

Since many contact sports or other activities produce collisions or impacts that produce cuts or wounds to the skin of the orbit and eyebrow region, the sweat diverting apparati 101, 201, 301, 401, 501, 701, 801 and 901 of the present invention provides a membrane that will protect the skin and dissipate or cushion any impact. Basketball, soccer and boxing are a few sports where cuts to the orbit area are common. Additionally, any time a hat or helmet is worn; it tends to keep body heat contained within the headwear and triggers the body to produce more sweat to regulate body temperature. The sweat diverting apparatus of the present invention could be worn in combination with separate headwear or eyewear and allow sweat to be automatically diverted without user intervention and assist in maintaining optimal visual clarity. This could be especially important if both hands are needs to perform a task: such as using surgical tools (surgeons are gowned and covered); using a chainsaw and wearing a hardhat; fighting fire with 60 pounds of protective gear on, including a helmet; firing a weapon, flying an aircraft, or driving military vehicles in hot climates, especially under combat conditions.

Figure 8:
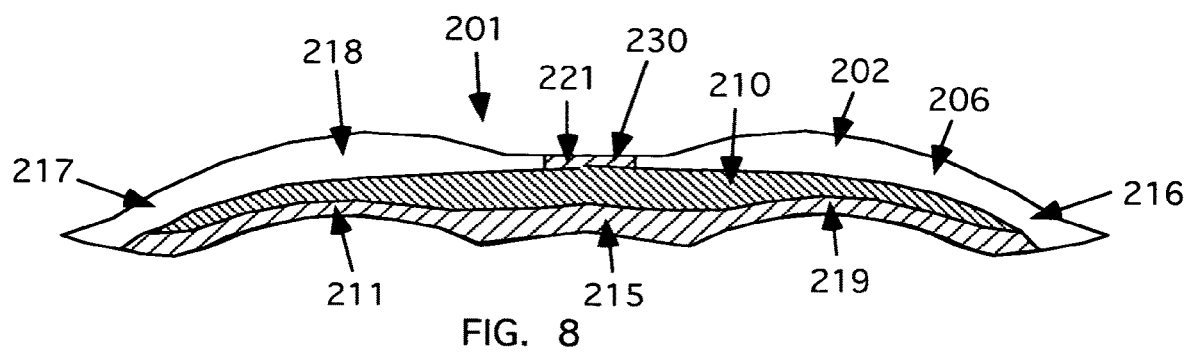
FIG. 8 is a rear view of the moisture diverting apparatus shown in FIG. 7.

FIG. 8 is a rear or inner view of the diverting apparatus 201 shown in FIG. 7 for spanning a large portion of the brow and/or lower forehead above both eyes. Diverting apparatus 201 comprises rear or inner surface 202 having portion including an adhesive surface or coating 211 for releasably attaching said diverting apparatus 201 to a body section adjacent a wearer's eye, adhesive-free portion 206 to divert, catch or collect sweat or moisture dripping from a forehead or brow, an intermediate or middle portion 221 having an adhesive 230 for releasably attaching the middle top portion of diverting apparatus 201 to the forehead or upper nose of the wearer to create a high spot so any sweat is directed to the side of the face and to assist in maintaining placement of said diverting apparatus 201 on the skin, side section 216, opposite side section 217, top section 218, bottom section 219, intermediate bridge section 215. Middle portion 221 may be fabricated without an adhesive surface or coating. A plurality of adhesive portions (not shown) may be placed on top section 218 in spaced-apart fashion to assist in securing diverting apparatus 201 to the wearer.

Figure 9A:
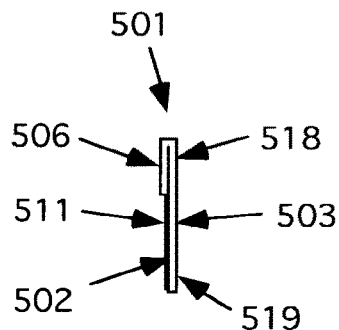
FIG. 9A is a side view of a moisture diverting apparatus shown with a folded upper portion.
Figure 10:
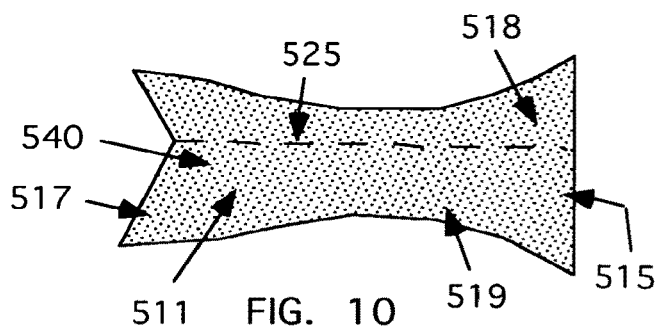
FIG. 10 is a rear view of the moisture diverting apparatus shown in FIG. 9A prior to folding the sections together.
Figure 11:
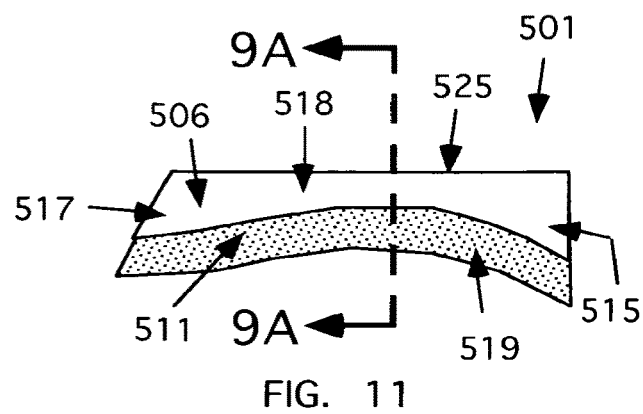
FIG. 11 is a rear view of the moisture diverting apparatus shown in FIGS. 9A and 10 after folding the sections together creating an adhesive portion and an adhesive free portion.

FIGS. 9A, 10 and 11 illustrate yet another embodiment of the present invention that may be fabricated from a single substrate. As shown in the drawings, FIG. 9A is a side view of FIG. 11 in axis 9A-9A, the diverting apparatus comprises a substrate 540 comprising an adhesive surface, film or coating 511 on a surface thereof. The diverting apparatus 501 is formed by cutting or otherwise forming substrate 540 into a desired pattern, such as, for example, as illustrated in FIG. 10. In one embodiment, the pattern is die cut from a larger substrate to form the desired pattern. Known molding or deposition techniques may also be used to form the desired pattern. When a desired pattern is formed, such as that shown in FIG. 10, an upper section 518 of substrate 540 is folded over, for example, along dotted line 525 to form diverting apparatus 501. As shown, diverting apparatus 501 has a folded upper section that creates an adhesive free upper portion 506, a lower portion 519 having exposed adhesive 511 for releasably attaching diverting apparatus 501 to the skin adjacent the eye or eyes, and an, adhesive-free outer face 503. Top portion 506 is designed to abut the eyebrow area and does not contain adhesive so the eyebrow hair will remain intact when sweat diverting apparatus 501 is removed from the skin. Folding the upper member 518 onto itself also doubles the wall thickness of upper section 518, (as an example from 7 mil to 14 mil) improving rigidity and creating a stronger protruding ledge or member that will better maintain structural integrity of protruding ledge for channeling liquid away from the eye under severe conditions or excessive sweating.

Although FIGS. 9A, 10 and 11 show the entire surface of substrate 540 having an adhesive, it is appreciated that the adhesive 511 may be selectively applied or patterned on portions of the substrate 540. For example, only a single layer of adhesive is required in the section of the upper fold section. Adhesive 511 may be patterned on substrate 540 prior to cutting so that a single layer of adhesive exists between the fold when it is created.

Sweat diverting apparatus 501, or any other embodiments disclosed herein, preferably comprise a material that does not absorb liquid. Sweat diverting apparatus of the present invention may comprise a variety of shapes including rectangular, arcuate, curved, longitudinal, or any other shape that will allow attachment to the skin above the eye or eyes.

FIG. 10 is a rear view drawing of the sweat diverting apparatus of FIG. 9A prior to folding and joining upper section 518 over to fabricate one piece apparatus 501 having outside section 515, opposite section 517, lower section 519 having adhesive 511, top section 518 having adhesive 511, fold line 525 (dotted line) for creating a surface having an adhesive-free portion adjacent to a portion 519 having adhesive and doubling the wall thickness of upper section 518 when joined together.

FIG. 11 is a rear view drawing of the one piece sweat diverting apparatus of FIGS. 9A and 10 ready for use fabricated from one piece of material having a folded upper section 518 that creates an adhesive free portion 506 adjacent lower portion 519 having adhesive 511 for removably attaching sweat diverting apparatus 501 to the skin adjacent an eye. Folded upper section 518 doubles the wall thickness adding strength and rigidity to the apparatus.

Figure 9B:
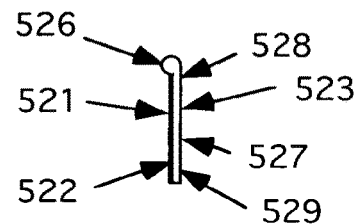
FIG. 9B is a side view of a moisture diverting apparatus shown with a bead or protrusion that can be fabricated by extrusion, stamping or other known manufacturing methods.
Figure 9D:
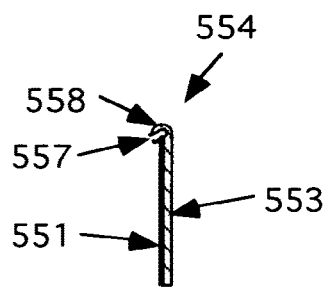
FIG. 9D is a side view of a moisture diverting apparatus having an enlarged upper edge comprising a channel with a plurality of perforations.
Figure 12:
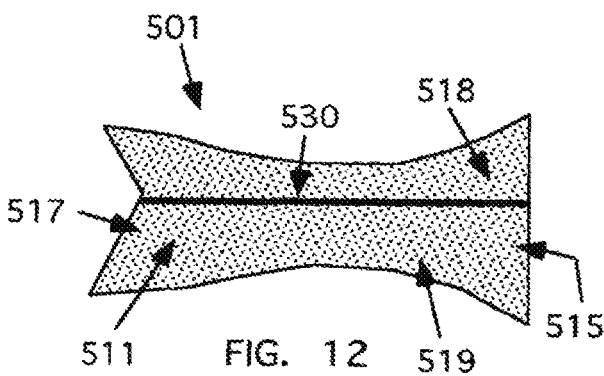
FIG. 12 is a rear view of a moisture diverting apparatus similar to FIG. 10 having a reinforcing member to assist in maintaining the shape of the apparatus.
Figure 9C:
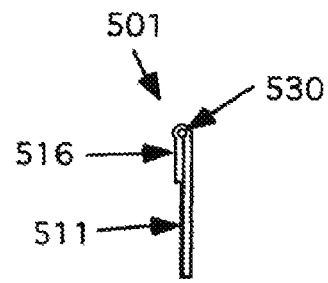
FIG. 9C is a side view of a moisture diverting apparatus in accordance with another embodiment of the present invention.

FIG. 12 is a rear view drawing of the sweat diverting apparatus of FIG. 9C or 10 prior to folding having a reinforcing member or wire 530 attached to adhesive 511 to assist in maintaining and customizing the shape of the sweat diverting apparatus 501. Sweat diverting apparatus 501 having outside section 515, opposite section 517, lower section 519 having adhesive 511, and top section 518.

Sweat diverting apparatus 501 may comprise a flexible material that contours to the individual shape of the wearer's face or orbit and may include reinforcing member 530 or other such members as mesh, strips, wires or the like to allow said sweat diverting apparatus to be "pre-shaped" prior to attachment and conform to the facial contour of each wearer. Although not necessary in practice, a shapeable sweat diverting apparatus having a "memory" would be more likely to maintain its shape or configuration and remain attached to the wearer as the weight of any sweat it may gather and divert increases.

FIG. 9B is a side view of another embodiment of the present invention. As shown, the sweat diverting apparatus includes a bead or enlarged portion 526 that contacts, or makes near contact to the brow region of a wearer. The sweat diverter comprises substrate 527 having adhesive-free outer face 523, top section 528, bottom section 529, back or inner surface 522 that includes an adhesive surface, film or coating 521 for releasably attaching the diverting apparatus to the skin adjacent the eye or eyes. The sweat diverter of FIG. 9B may be a one piece construction or constructed from multiple components that are bonded, or otherwise attached. The diverting apparatus of FIG. 9B may be fabricated by extrusion, stamping, or other known manufacturing methods.

Bead or enlarged portion 526 acts to form a channel between itself and the lower brow region of the wearer or alternatively, or in combination, acts to wick moisture from the lower brow region via capillary action or gravity away from the eye. Enlarged portion or bead 526 may contain one or more grooves or channels extending along its length, or a portion thereof that may be useful in facilitating the transport of moisture droplets away from the eye.

FIG. 9C is a side view drawing of the sweat diverting apparatus of FIG. 12, and similar to those illustrated in FIGS. 9A and 9B. As shown, a member 530, such as a fiber, wire, or other elongate member is positioned within a folded upper section 516 that encases or envelopes member 530. Member 530 may be a reinforcing member for maintaining and customizing the shape of the sweat diverting apparatus 501.

FIG. 9D is a side view drawing of a sweat diverting apparatus 554 having a channel 558 with a plurality of perforations 557 for collecting and diverting liquid from the brow of the wearer. Sweat diverting apparatus 554 having an adhesive portion 551 on rear surface 552 for selectively attaching to the skin, a front surface 553 that is adhesive free.

Figure 13:
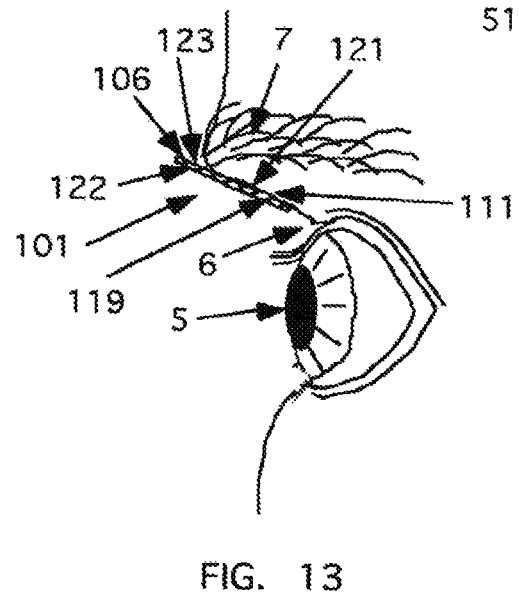
FIG. 13 is a cross sectional side view of a moisture diverting apparatus attached to the wearer, having a protruding ledge in the region of the brow line for diverting liquid or sweat away from the eye or eyes.

FIG. 13 shows a cross sectional side view of a sweat diverting apparatus 101 attached to the wearer, having a lower section 119, and an upper portion 118 that includes a protruding member or ledge 122 formed by attaching the sweat diverting apparatus 101 to the skin below brow line 7 for diverting liquid or sweat away from the eye or eyes 5. Protruding ledge 122 creates channel, trough or gutter 123 for gathering and diverting liquid or sweat away from the eye or eyes 5. Sweat diverting apparatus 101 having an adhesive portion 111 creating a liquid-tight seal 121 for attachment to the skin above eye lid 6, and an adhesive-free, longitudinal portion 106 on upper section 118 that keeps the eyebrow hair intact when sweat diverting apparatus 101 is selectively removed. As with many embodiments of the present invention, the width of protruding member 122 can be increased to assist in shading the eye.

Similarly stated, longitudinal portion 106 of diverting strip 101 comprises an adhesive-free portion creating a small protruding lip or ledge 122 fashioning a small channel 123 above the liquid tight sealing portion 121 of the diverting strip or membrane 101 that has adhesive on the lower portion 111. When sweat rolls down the forehead, the small protruding lip or ledge 122 catches and channels the sweat to the side of the eye or eyes.

Figure 14:
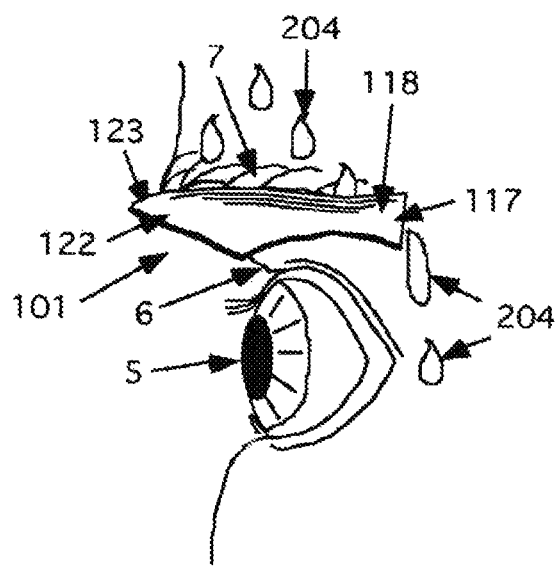
FIG. 14 is a side isometric view of the moisture diverting apparatus of FIG. 13 attached to the wearer, showing sweat, rain drops or other moisture droplets dripping from the forehead and being diverted away from the eye.

FIG. 14 is an isometric side view of the sweat diverting apparatus of FIG. 13 attached to the wearer above eyelid 6, showing sweat being diverted away from the eye 5. Sweat diverting apparatus 101 having protruding ledge 122 creating channel, trough or gutter 123 at brow line 7 for gathering, moving and diverting liquid or sweat away from the eye or eyes 5.

Sweat diverting apparatus 101 may be comprised of an absorbent material that may also include adhesive properties. The sweat diverting apparatus 101 may comprise a flexible structural material or a rigid structural material. The rigid structural properties may be either longitudinal (lengthwise) and/or latitudinal (height wise) relative the shape of the sweat diverting apparatus.

Figure 15:
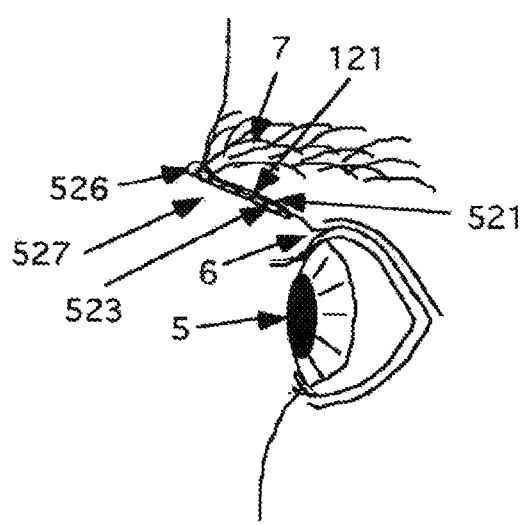
FIG. 15 is a cross sectional side view of a moisture diverting apparatus of the present invention attached to the wearer having a bead or enlarged portion for gathering and diverting sweat or other forms of moisture from the brow region of the wearer.

FIG. 15 is a cross sectional side view of the sweat diverting apparatus 527 of FIG. 9B attached to the wearer, having a lower section 523, and an upper section 526 that includes a bead or enlarged member 526 for contacting or making near contact with the skin below brow line 7 for diverting liquid or sweat away from the eye or eyes 5.

Figure 16:
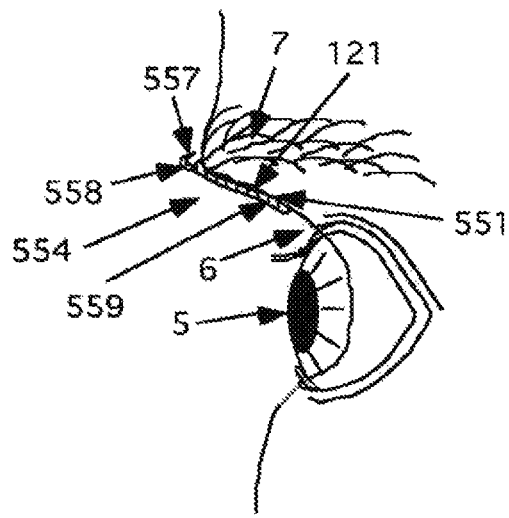
FIG. 16 is a cross sectional side view of a moisture diverting apparatus of the present invention attached to the wearer showing a hollow tube having a plurality of perforations portion for gathering and diverting moisture and the like from the brow region of the wearer

FIG. 16 is a cross sectional side view of the sweat diverting apparatus 554 of FIG. 9D attached to the wearer, having a hollow tube 558 containing a plurality of perforations 557 for gathering and diverting sweat from the brow 7 of the wearer.

Figure 17:
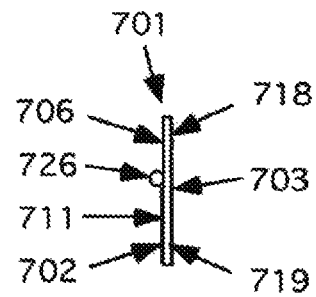
FIG. 17 is a side view of a moisture diverting apparatus of the present invention having a member for wicking liquid away from an eye or the eyes.

FIG. 17 is a side view of a sweat diverting apparatus in accordance with another embodiment of the present invention. As shown, diverter 701 includes an absorbent member or string 726 to assist in wicking liquid laterally to the side of the face. Sweat diverting apparatus 701 comprises adhesive-free outer face 703, top section 718, bottom section 719, back or inner surface 702 that includes a lower adhesive coated surface, film or coating 711 for releasably attaching diverting apparatus 701 to the skin adjacent the eye or eyes. Top portion 706 is designed to abut the eyebrow area and does not contain adhesive so the eyebrow hair will remain intact when sweat diverting apparatus 701 is removed from the skin.

Figure 19:
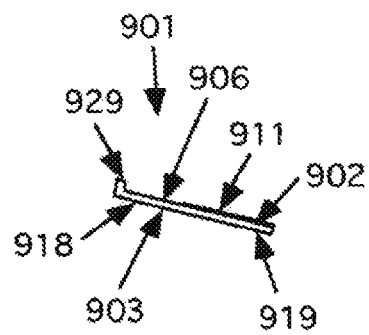
FIG. 19 is a side view of a moisture diverting apparatus of the present invention having a raised lip or member to assist in diverting liquid away from an eye or the eyes.
Figure 18:
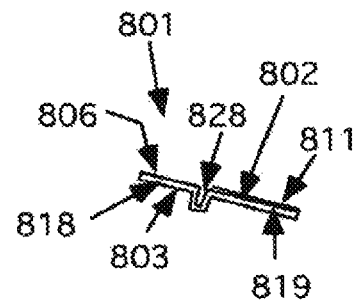
FIG. 18 is a side view of a moisture diverting apparatus of the present invention having a recessed channel or groove for diverting liquid away from an eye or the eyes.
Figure 20:
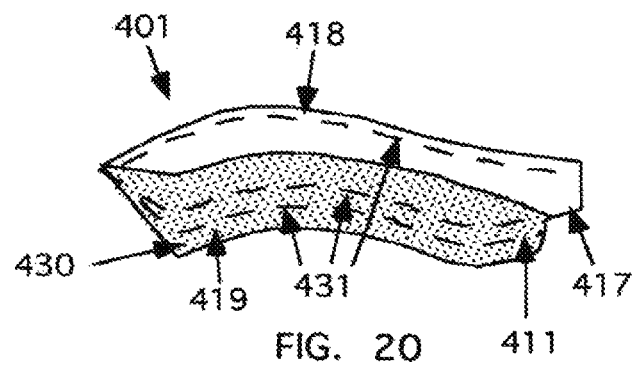
FIG. 20 is a rear view of a moisture diverting apparatus of the present invention having a frangible portion(s) or lines for sizing the apparatus to fit a variety of different sized individuals.

FIG. 18 is a side view of yet another embodiment of the present invention wherein sweat diverting apparatus 801 includes a recessed, preformed channel or groove 828 to assist in diverting or moving liquid laterally to the side of the face. Sweat diverting apparatus 801 of the present invention comprises adhesive-free outer face 803, top section 818, bottom section 819, back or inner surface 802 that includes a lower adhesive coated surface, film or coating 811 for releasably attaching diverting apparatus 801 to the skin adjacent the eye or eyes. Top portion 806 is designed to abut the eyebrow area and does not contain adhesive so the eyebrow hair will remain intact when sweat diverting apparatus 801 is removed from the skin FIG. 19 is a side view of a sweat diverting apparatus of the present invention that includes a raised lip or protrusion 929 at top of the upper section 918 to assist in preventing liquid or sweat from dripping out of the front of sweat diverting apparatus during use. Sweat diverting apparatus 901 of the present invention comprises adhesive-free outer face 903, top section 918, bottom section 919, back or inner surface 902 that includes a lower adhesive coated surface, film or coating 911 for releasably attaching diverting apparatus 901 to the skin adjacent the eye or eyes. Top portion 906 is designed to abut the eyebrow area and does not contain adhesive so the eyebrow hair will remain intact when sweat diverting apparatus 901 is removed from the skin FIG. 20 is a rear view of a sweat diverting apparatus of the present invention having one or more frangible portion or imprinted lines for sizing the apparatus to fit a variety of different sized individuals. Sweat diverting apparatus 401 comprises a an adhesive-free top section 418 and a bottom section 419 having adhesive 411. In one embodiment one or more perforating or scoring lines 431 are provided that permits the user to selectively size or shape the diverting apparatus prior to attachment. FIG. 20 shows an example of where lines 431 may be placed. However, it is appreciated that lines 431 can be formed in any location that permits the user to adjust one or more of the width, length, contour, shape, etc. of diverting apparatus 401. In lieu of, or in combination with perforating or scoring lines, imprinted lines may be provided to assist the user in manually cutting the diverter to a size and shape most appropriate for the user.

The eyes of humans are recessed relative to the eyebrow and forehead and the ability to custom shape the sweat diverting apparatus 101, 201, 301, 401, 501, 701, 801, and 901 to fit each individual wearer will add the comfort of using the invention. As described above this can be accomplished individually by the wearer cutting the diverting apparatus or by a series of perforations 431 manufactured in the diverting apparatus that allow the user to peel portion 430 away to customize the size. A separate, removable liner may also be used to keep the adhesive surface fresh. A plurality of diverting apparati can be ganged, rolled or stacked together so the adhesive surface is removably attached to the non-adhesive surface of the underlying and adjacent diverting apparatus. This way, one diverting apparatus can be peeled from a multitude of sweat diverting strips.

A number of embodiments have been disclosed herein as they relate to the sweat diverting apparatus of the present invention. It is important to understand that many of the elements described herein may be interchangeable. It is also important to note that the invention can comprise a variety of embodiments, ranging from a single piece fabrication, where the components or apparatus are manufactured unitarily, to a plurality of components all that achieve the desired result of safely preventing sweat or moisture from entering the eye or eyes.

What is claimed is:

1. A method for maintaining visual clarity of a human wearer by diverting perspiration that rolls down a forehead of the human wearer away from an eye of the human wearer to a side of the human wearer's face with a perspiration diverting apparatus that is configured to be worn entirely above an upper eyelid of the eye, the perspiration diverting apparatus configured as a substrate having a bottom section shaped to conform to a contour of an upper orbit of the eye above the eye of the human wearer, one portion of the bottom section having an adhesive inner surface for releasable attachment to the upper orbit of the eye below an eyebrow and entirely above the upper eyelid of the eye of the human wearer, and an upper section free of adhesive, visual clarity of the human wearer is maintained when the perspiration diverting apparatus is worn by the human wearer, said method comprising:
    adhering the perspiration diverting apparatus to an area above the upper eyelid and below the eyebrow of the human wearer via the adhesive inner surface disposed on the one portion of the bottom section of the substrate such that the upper section extends upward from the bottom section and away from skin of the human wearer to create a gutter directly below or along the eyebrow of the human wearer to the side of the face of the human wearer and such that an entirety of the perspiration diverting apparatus resides above the upper eyelid and at or below the eyebrow of the human wearer; and
    collecting perspiration that rolls down the forehead of the human wearer in the gutter to cause the gutter to divert the collected perspiration along the gutter to the side of the face of the human wearer.

2. A method for maintaining visual clarity of a human wearer by diverting perspiration that rolls down a forehead of the human wearer away from an eye of the human wearer to a side of a face of the human wearer, said method comprising:
    providing a perspiration diverting apparatus that is configured to be worn entirely above an upper eyelid of the eye, the perspiration diverting apparatus comprising a substrate including:
        a bottom section shaped to conform to a contour of an upper orbit of the eye, one surface of the bottom section having an adhesive for releasable attachment to the upper orbit of the eye above the upper eyelid of the eye and below an eyebrow of the human wearer; and
        an upper section free of adhesive;
    adhering the perspiration diverting apparatus to an area above the upper eyelid of the eye and below the eyebrow of the human wearer via the adhesive disposed on the one surface of the bottom section of the substrate such that the upper section extends upward from the bottom section and away from skin of the human wearer to create a gutter directly below or along the eyebrow of the human wearer to the side of the face of the human wearer and such that an entirety of the perspiration diverting apparatus resides above the upper eyelid and at or below the eyebrow of the human wearer; and
    collecting perspiration that rolls down the forehead of the human wearer in the gutter to cause the gutter to divert the collected perspiration away from the eye along the gutter to the side of the human wearer's face,
    visual clarity of the human wearer is maintained when the perspiration diverting apparatus is worn by the human wearer.

3. A method for maintaining visual clarity of a human wearer by diverting perspiration that rolls down a forehead of the human wearer away from an eye of the human wearer to a side of a face of the human wearer, said method comprising:
    providing a perspiration diverting apparatus that is configured to be worn entirely above an upper eyelid of the eye, the perspiration diverting apparatus comprising a substrate;
    configuring a lower section of the substrate to conform to a contour of an upper orbit of the eye, providing an interior surface of the lower section as an adhesive for releasable attachment to the upper orbit of the eye above the eyelid of the eye and below an eyebrow of the human wearer;
    providing an upper section of the substrate free of adhesive;
    adhering the perspiration diverting apparatus to an area above the upper eyelid of the eye and below the eyebrow of the human wearer via the interior surface adhesive of the lower section of the substrate such that the upper section extends upward from the lower section and away from skin of the human wearer to create a gutter extending directly below or along the eyebrow of the human wearer to the side of the face of the human wearer and such that an entirety of the perspiration diverting apparatus resides above the upper eyelid and at or below the eyebrow of the human wearer; and
    collecting perspiration that rolls down the human wearer's forehead in the gutter and diverting the collected perspiration along the gutter away from the eye to the side of the human wearer's face,
    visual clarity of the human wearer is maintained when the perspiration diverting apparatus is worn by the human wearer.

* * * * *